United States Patent [19]
Hall et al.

[11] Patent Number: 5,969,215
[45] Date of Patent: Oct. 19, 1999

[54] METHOD OF PLANT TISSUE CULTURE AND REGENERATION

[75] Inventors: Robert David Hall, Wageningen; Franciscus Andries Krens, Veenendaal; Henricus Adrianus Verhoeven, Breugel; Maria Colijn-Hooymans, Bennekom, all of Netherlands; James Martin Dunwell, Henley-on-Thames, United Kingdom; Guy Weyens, Beersel, Belgium

[73] Assignee: Zeneca Limited, London, United Kingdom

[21] Appl. No.: 08/615,216

[22] PCT Filed: Oct. 14, 1994

[86] PCT No.: PCT/GB94/02252

§ 371 Date: Mar. 14, 1996

§ 102(e) Date: Mar. 14, 1996

[87] PCT Pub. No.: WO95/10178

PCT Pub. Date: Apr. 20, 1995

[30] Foreign Application Priority Data

Oct. 14, 1993 [GB] United Kingdom .................. 9321183

[51] Int. Cl.⁶ .................................................. C12N 15/00
[52] U.S. Cl. ............................................................ 800/278
[58] Field of Search ................................ 435/172.3, 420, 435/421, 430, 430.1; 800/205, DIG. 71

[56] References Cited

U.S. PATENT DOCUMENTS

| | | | |
|---|---|---|---|
| 4,945,050 | 7/1990 | Sanford et al. | 435/172.1 |
| 5,204,253 | 4/1993 | Sanford et al. | 435/172.3 |
| 5,302,523 | 4/1994 | Coffee et al. | 435/470 |
| 5,508,189 | 4/1996 | Tallman | 435/240.5 |

FOREIGN PATENT DOCUMENTS

| | | |
|---|---|---|
| 0 517 833 | 9/1991 | European Pat. Off. . |
| 3-103183 | 4/1991 | Japan . |
| 91/13159 | 9/1991 | WIPO . |

OTHER PUBLICATIONS

D'Halluin, K., et al., Bio/Technology, "Transformation of Sugarbeet (*Beta vulgaris* L.) and Evaluation of Herbicide Resistance in Transgenic Plants", vol. 10, 1992, pp. 309–314.

Frearson, E. M., et al., Developmental Biology, "The Isolation, Culture and Regeneration of Petunia Leaf Protoplasts", vol. 33, 1973, pp. 130–137.

Hall, Robert D., et al., Plant Cell Reports, Improvement of protoplast culture protocols for *Beta vulgaris* L. (sugar beet), vol. 12, 1993, pp. 339–342.

Harms, C. T., et al., Plant Cell Tissue Organ Culture, "Clonal propagation in vitro of red beet (*Beta vulgaris* ssp.) by multiple adventitious shoot formation", vol. 2, 1983, pp. 93–102.

Kaeppler, H. F., et al., Plant Cell Reports, "Silicon carbide fiber–mediated DNA delivery into plant cells", vol. 9, 1990, pp. 415–418.

Kao, K.N., et al., Planta (Berl.), "Nutritional Requirements for Growth of *Vicia hajastana* Cells and Protoplasts at a Very Low Population Density in Liquid Media," vol. 126, 1975, pp. 105–110.

Krens, F. A., et al., Theor. Appl., Genet., "Transfer of cytoplasm from new Beta CMS sources to sugar beet by asymmetric fusion", vol. 79, 1990, pp. 390–396.

Krens, F. A., et al., Nature, "In vitro transformation of plant protoplasts with Ti–plasmid DNA," vol. 296, pp. 72–74 (1982).

Kruse, T., et al., Plant Physiol., "Isolation of Guard Cell Protoplasts from Mechanically Prepared Epidermis of *Vicia faba* Leaves", vol. 90, 1989, pp. 1382–1386.

Leduc, N., et al., Sex Plant Reprod., "Gene transfer to inflorescence and flower meristems using ballistic micro––targeting", vol. 7, 1994, pp. 135–143.

Mawson, B. T., Plant, Cell And Environment, "Modulation of photosynthesis and respiration in guard and mesophyll cell protoplasts by oxygen concentration", vol. 16, 1993, pp. 207–214.

Mawson, B. T., Planta, "Regulation of blue–light–induced proton pumping by *Vicia faba* L. guard–cell protoplasts: Energetic contributions by chloroplastic and mitochondrial activities", vol. 191, 1993, pp. 293–301.

Murashige, T., et al., Physiologia Plantarum, "A Revised Medium for Rapid Growth and Bio Assays with Tobacco Tissue Cultures", vol. 15, 1962, pp. 473–495.

Pedersen, C., et al., Plant Science, "Petioles as the tissue source for isolation and culture of *Beta vulgaris* and *B. maritima* protoplasts", vol. 95, 1993, pp. 89–97.

Potrykus, I., Plant Breeding: Principles And Prospects, "Gene transfer to plants: approaches and available techniques", 1993, pp. 126–137.

Schneider, I., et al., Biochem. Physiol. Pflanzen, "Adventitious Shoot Formation in a Tissue Culture Line of Sugarbeet", vol. 182, 1987, pp. 485–490.

Talbot, L. D., et al., Plant Physiol., "Sugar and Organic Acid Accumulation in Guard Cells of *Vicia faba* in Response to Red and Blue Light", vol. 102, 1993, pp. 1163–1169.

Tran Thanh Van, K., Advances in Biochemical Engineering, "Control of Morphogenesis or What Shapes a Group of Cells?", vol. 18, Plant Cell Cultures II, 1980, pp. 152–171.

Weyers, J. D. B., et al., Longman Scientific & Technical, "Methods in Stomatal Research", Longmans, London, 1990, p. 3.

(List continued on next page.)

Primary Examiner—Bruce R. Campell
Attorney, Agent, or Firm—Liza D. Hohenschutz

[57] ABSTRACT

Plants may be regenerated from stomatal cells or protoplasts of such cells. Prior to regeneration the cells or protoplasts may be genetically transformed by the introduction of hereditary material most preferably by a DNA construct which is free of genes which specify resistance to antibiotics. The regeneration step may include callus formation on a hormone-free medium. The method is particularly suitable for sugar beet.

13 Claims, No Drawings

OTHER PUBLICATIONS

Zeiger, E., et al., Science, "Longevity of Guard Cell Chloroplasts in Falling Leaves: Implication for Stomatal Function and Cellular Aging", vol. 218, 1982, pp. 680–682.

Zeiger, E., et al., Stomatal Function, "The Blue–Light Response of Stomata: Mechanism and Function," Stanford University Press, Stanford, CA, 1987, pp. 209–227.

P Sahgal et al (1993) Plant Physiology 102 (supp):31.

J–P Bourgin (1979) Physiologia Plantarum 45: 288–292.

Sahgal, et al: "Regeneration of plants from cultured guard cell protoplasts of Nicotiana glauca (Graham)", Plant Science, vol. 97, 1994, Ireland, pp. 199–208.

Kotowska et al: "Preliminary report on epidermis culture of sugar beet", Bulletin of the Polish Society of Sciences, Biological Sciences, vol. 32 11/12, 1984, pp. 435–437.

De Greff et al: "In vitro culture of the sugarbeet: description of a cell line with high regeneration capacity", Plant Science Letters, vol. 17, 1979, North–Holland, pp. 55–61.

Y.P.S. Bajaj–Ed "Biotechnology in agriculture and forestry, vol. 23, Plant protoplasts and genetic engineering IV", 1993, Springer Verlag, Berlin, Chapter II2, pp. 147–169, Lindsey et al: "Transformation in sugarbeet (Beta vulgaris L.)", p. 149, line 4—p. 150, line 9.

Kaeppler et al: "Silicon carbide fiber–mediated stable transformation of plant cells", Theoretical And Applied Genetics, vol. 84, 1992, pp. 560–566.

Cupples et al: "Division of guard cells protoplasts of Nicotianan glauca (Graham) in liquid cultures", Plant, Cell and Environment, vol. 14, 1991, pp. 691–697.

Y.P.S. Bajaj–Ed–"Biotechnology in agriculture and forestry vol. 2 Crops I.", 1985, Springer Verlag, Berlin, chapter II.12, pp. 462–470, A.I.Atanassov: "Sugar beet (*Beta vulgaris* L.)", p. 467, line 25—p. 468, line 28.

Iglesias et al: "Transient expression of visible marker genes in meristem cells of wheat embryos, after ballistic micro-–targetting", Planta, vol. 192, 1994, Berlin, pp. 84–91.

Kotowaka: "Morphogenetische Fahigkeiten des Blutenstandsgetriebwebes bei Zuckerruben in In–vitro–Kutluren: II. Die Teilung und Differzierung der Zellen", Beitrage Biologische Pflanzenzuchtung, vol. 67, No. 2, 1992, pp. 209–223.

Evans et al: —EDS–"Handbook of plant cell culture, vol. 4, Techniques and applications", 1986, chapter 23, pp. 652–680, A.I.Atanassov: "Sugar–beet".

Forti et al: "Callus and cell culture in sugarbeet", Acta Horticulturae Proc. 1st,Ishs Symp. in vitro Culture & Hortic. Breeding, vol. 280, 1990, pp. 271–276.

T E Weier et al (1982) Botany p. 184.

K Esau (1965) Plant Anatomy p. 8.

METHOD OF PLANT TISSUE CULTURE AND REGENERATION

This application claims benefit of international application PCT/GB94/02252, filed Oct. 14, 1994.

BACKGROUND OF THE INVENTION

This invention relates to a method of plant tissue culture and regeneration. More particularly the invention relates to a method for the genetic transformation of plant cells, the regeneration of whole plants from such cells and the plants so produced. Particularly, but not exclusively, the invention relates to a method for the transformation of *Beta vulgaris*, which includes sugar beet, fodder beet, table beet and Swiss chard.

Although genetic transformation and subsequent regeneration is largely a matter of routine nowadays for many plants species, some species have remained recalcitrant to transformation by most of the numerous methods which are available. *Beta vulgaris* is one such example where, despite transient expression in some cells and occasional success with specific genotypes, no simple routine method is available for the production of transgenic plants (International Patent Application No. WO 91/13159; D'Halluin, K. et.al., Biotechnology 10 309–314 (1992)). More particularly, no method for transformation via direct gene transfer and subsequent regeneration has yet been published. The recalcitrance of sugar beet protoplasts is well documented (Lindsey et.al. Transformation in Sugar Beet (*Beta vulgaris* L.) Biotechnology in Agriculture and Forestry, Vol 23, Plant protoplasts and Genetic Engineering IV" Y. P. S. Bajaj, Ed., Springer-Velag, Berlin, 1993). Cell division in vitro is restricted and totipotent colonies are generally obtained only at low frequency (0.1% or less). Protoplasts isolated from sugar beet leaves vary in size and morphology, reflecting the high degree of cellular heterogeneity present within the source tissue both at physiological (resulting from the relative location of the cells in vivo) and cytogenetic (ploidy, cell cycle phase) levels.

There is, therefore, a continuing need for a simple, high frequency transformation method which may be applicable to beet.

In order that a cell may be efficiently transformed, certain requirements must be satisfied. First the gene to be inserted must be assembled within a construct which contains effective regulatory elements which will drive transcription of the gene. Next, there must be available a method of transporting the construct into the cell. Once the construct is within the cell membrane, integration into the endogenous chromosomal material either will or will not occur. The probability of integration may be improved by certain means but, in general, integration is simply a matter of uncontrolled chance. Finally, as far as plants are concerned the target cell type must be such that cells can be regenerated into whole plants.

Plant cells are more difficult to transform than bacterial or animal cells because the presence of hard cell walls presents a barrier to insertion of the construct through that wall.

Thus the choice of method for the transformation of plant cells tends to be limited to those which are convenient for the target plant type (Potrykus, I, in Plant Breeding: Principles and Prospects, Ed. Hayward et.al., Publ. Chapman & Hall, London (1993)). As a generalisation, dicotyledonous plants are relatively easy to transform whereas monocotyledonous plants are very difficult, there being only a few techniques available in respect of which success has been reported, and that with very low success rate.

One method which is claimed to transform plant cells is the procedure known as "microinjection" where, under the microscope, a DNA construct is injected from a hollow needle into a target cell. A variant of that procedure is the rupturing of the cell wall with a needle, the DNA being added to the surrounding medium and allowed to diffuse into the cell through the break in the cell wall. This variant is known as "micropricking". Both of these procedures require a high degree of manipulative skill by the operator and are very time consuming. Japanese Published Patent Application Number 03103183 of 1991 proposes that a foreign gene may be inserted into plant cells by microinjection into guard cells which occur in the epidermal tissue of a plant, followed by culture of those cells. However, physiological studies of guard cells have shown that they have abnormally high intracellular pressures and it is reasonable to question whether microinjection of DNA into guard cells is feasible and, in any case this method would suffer from the principal drawback of microinjection which is that the process is so time-consuming that only a relatively small number of cells can be injected in the course of a day. No data were presented which accurately describe the isolation of transgenic plants by this route.

It is probably true to say that to date the most effective methodology for the introduction of gene constructs, particularly for monocotyledonous cells has been the so-called "biolistics" method in which high density metallic particles, usually of tungsten or gold, are coated with the gene construct and are propelled by an explosive release of gas at a target cell culture. This alternative approach abandons the high precision of targeting which is inherent in microinjection and micropricking, in favour of a rapid "pepperpot" approach which enables large numbers of cells to be "hit" in a short time, giving a large number of putative transformants for screening.

Effective though the biolistic method may be, it requires expensive hardware and, although rapid by comparison with some other methods which have been attempted, is time-consuming. It does, however, achieve high numbers of transformation events at each bombardment. One problem with this technique is the effect of the blast of expanding gas on the target tissue. Another is the difficulty of aiming the projectile shower at a selected area of the target. Various microtargeting devices have been designed to help overcome this latter problem (Leduc et.al., Sex.Plant Reprod., 7, 135–143 (1994); Iglesias et.al., Planta, 192, 84–91 (1994)) but to date no transgenic plants have been produced.

Mixing of plant cells with plasmid DNA and sub-micron diameter fibres or whiskers is a simple and inexpensive alternative transformation method. There have been several published reports of transformation using silicon carbide whiskers. The first described transient expression of β-glucuronidase (gus) in Black Mexican Sweet (BMS) corn suspension cells (Kaeppler et al., 1990). The same group have recently published their results on stable transformation of BMS and tobacco (Kaeppler et al., 1992). In the corn system a mean of 3.4 BASTA-resistant BMS colonies were recovered from each vortex-treated sample of cells (300 μl packed cell volume) using a BAR and gus-containing plasmid. Sixty five per cent of these herbicide-resistant colonies expressed gus. (Kaeppler H. F., Gu W., Somers D. A., Rines H. W, Cockburn A. F. (1990) "Silicon carbide fiber-mediated DNA delivery into plant cells", Plant Cell Reports 9: 415–418, and, Kaeppler H. F., Somers D. A., Rines H. W., Cockburn A. F. (1992), "Silicon carbide fiber-mediated stable transformation of plant cells", Theor. Appl. Genet. 84: 560–566. The use of whiskers for the transformation of plant cells, particularly maize, is the subject of U.S. Pat. No. 5,302,523 in the name of Zeneca Limited.

There are numerous factors which influence the success of transformation. The design and construction of the exogenous gene construct and its regulatory elements influence the integration of the exogenous sequence into the chromosomal DNA of the plant nucleus and the ability of the transgene to be expressed by the cell. A suitable method for introducing the exogenous gene construct into the plant cell nucleus in a non-lethal manner is essential. Importantly, the type of cell into which the construct is introduced must, if whole plants are to be recovered, be of a type which is amenable to regeneration, given an appropriate regeneration protocol.

BRIEF SUMMARY OF THE INVENTION

The present invention is concerned with the selection of a particular cell type which is capable of regeneration.

An object of the present invention is to provide a method for plant transformation, particularly, but not exclusively, for sugar beet.

According to the present invention there is provided a method of producing a plant, comprising culturing a plant cell in a regeneration medium, characterised in that the said cell is a stomatal cell.

Preferably the said stomatal cell is subjected to regeneration in an intact organ containing said cells, however, the said cells may be isolated first.

One preferred source of stomatal cells is an isolated leaf epidermis.

The method of this invention is particularly applicable to plants of the species *Beta vulgaris* and especially to sugar beet.

Preferably the regeneration procedure includes the production of callus on a medium which is free of hormones.

The invention also provides a method for the genetic transformation of plants comprising introducing an hereditary material into a cell of the said plant and regenerating whole plants from the transformed cell, characterised in that the said cells are stomatal cells.

The transformation may be conducted on intact tissue containing stomata, one preferred tissue being senescent leaf tissue.

In a preferred embodiment the stomatal cells are those found in leaf epidermis.

The tissue containing stomatal cells may be macerated to produce a cell suspension from which plants are regenerated.

It is further preferred that the stomatal cells be converted to protoplasts prior to regeneration.

In a preferred embodiment the said hereditary material is a DNA construct which includes a selectable marker gene which does not specify resistance to an antibiotic and the transformed tissue is exposed to the appropriate selective agent.

The transformation may be conducted on a cell population containing guard cells or a cell population enriched in guard cell concentration.

The transformation may be conducted on a cell suspension.

The stomatal cells may be converted into protoplasts by enzymatic digestion of the cell wall before or after transformation.

One preferred transformation method comprises mixing a suspension of stomatal cells with a microscopic fibrous material and agitating same in the presence of the hereditary material.

DETAILED DESCRIPTION OF THE INVENTION

Within the epidermal layer of leaves, stems and certain reproductive tissue such as anthers (Kendra G., Phyton, 4, 83–96 (1952)), a certain type of specialised cells, known as Guard Cells, occur. Also, as leaves senesce other cells types tend to die earlier than guard cells (Zeiger E. and Schwartz A., Science 218, 680–682 (1982)). Therefore, senescent leaves represent a particularly enriched source of viable guard cells. Guard cells control the aperture of the leaf pores or stomata (for a review, see "Stomatal Function", ed. Zeiger et.al., 1987) Methods exist for the isolation of guard cells (see, for example Kruse et.al., Plant Physiology, 90, 1382–1386 (1989) and for their conversion to protoplasts (see, for example Mawson, B. T., Plant Cell Environment 16 207–214 (1993)) although these methods have been developed for use in physiological studies and commonly use the plant *Vicia faba* (Mawson, B. T. Planta, 191, 293–301, (1993); Talbott and Zeiger, Plant Physiology, 102, 1163–1169 (1993)). Guard cells are small, uniquely shaped cells with walls which are relatively thicker, harder and have a higher pectin content than other leaf cells. The stomatal pore is formed between two guard cells. There are two basic forms, the elliptical and the graminaceous forms. The term "stoma" and "stomata" are commonly used to refer not only to the pores but to the guard cells and the adjacent cells that form the stomatal complex (Weyers and Meider, in "Methods in Stomatal Research" page 3, Longmans, London, 1990). In this application we use the term "guard cell" to mean any cells involved in forming the stomatal complex.

It had long been believed that guard cells are not capable of division in culture (Tran Thanh Van, K., "Control of Morphogenesis or what shapes a group of cells" in Advances in Biochemical Engineering, Vol 18, Plant Cell Cultures II, Ed. A. Feichter, Publ. Springer-Verlag, Berlin, pages 151–171 (1980)) but recent work has shown, at least in respect of one species, *Nicotiana glauca,* that this is not so (Cupples, W. et.al.; Plant, Cell and Environment (1991), 14, 691–697) and that whole plants can be regenerated from tobacco guard cell protoplasts (Sahgal, P. et.al.; Plant Science 97, 199–208 (1994)). Tobacco is widely used as a model plant in plant science and one of its characteristics which makes it useful as a model system, is its propensity to regenerate from almost any cell type. Therefore, the ability of tobacco guard cells to regenerate to whole plants is not entirely surprising and the fact that tobacco has this ability does not necessarily indicate that other species will possess the same property.

There are two brief descriptions in the literature relating to callus production from epidermal cells of sugar beet (Kotowska and Rogozinska, Bull. of the Polish Acad. Sc., 32, 11–12 (1984); Kotowska, Beitr.Biol.Pflanz., 67, 209–223 (1992) and several reports (for example, Harms et.al., Plant Cell Tissue Organ Culture, 2, 93–102 (1983; Schneider and Gunther, Biochem.Physiol.Pflanzen, 182, 485–490 (1987)) of adventitious bud production on the epidermis of petioles. In no case was any evidence presented to show that guard cells were capable of division and callus production.

In one embodiment of the invention, leaf tissue, or the epidermal layer thereof, is macerated and digested to form a culture which contains the guard cells, the cells walls are digested to form protoplasts, the protoplasts are genetically transformed using an appropriate method, transformants are selected and plants regenerated from the transformants.

In another embodiment, leaf cells are transformed in situ by bombardment of the intact leaf tissue with microparticles coated with the exogenous DNA construct. The bombarded tissue is then macerated and guard cells, which are much more resilient that other cells types are recovered and whole plants regenerated therefrom.

In yet another embodiment leaf tissue is macerated and a cell population enriched in guard cells is prepared therefrom. Transformation is then performed on the enriched cell population and whole plants regenerated therefrom. The guard cells may be converted to protoplasts prior to transformation. In an alternative method pieces of epidermis may be manually peeled and callus produced therefrom.

It is the remarkable resilience of guard cells, along with the unexpected totipotency of the cells and their protoplasts compared with other cell types, which make them particularly suitable for use in either somatic hybridisation, cybrid production (Krens et.al., Theor.Appl.Genet., 79, 390–396, (1990) or transformation. However, that resilience would normally be viewed as a potential barrier to introduction of DNA into the cells. By this invention it has been demonstrated that guard cells can indeed be transformed and that the transformed cells can subsequently be regenerated, thus providing an effective method for the production of transgenic plants.

One important aspect of this invention is its applicability to the transformation of beet (*Beta vulgaris*), a species which has hitherto only been transformable at an unacceptably low frequency (Lindsey et.al. Transformation in Sugar Beet (*Beta vulgaris* L.), in Biotechnology in Agriculture and Forestry, Vol 23, "Plant protoplasts and Genetic Engineering IV" Y. P. S. Bajaj, Ed., Springer-Velag, Berlin, 1993).

The procedure of the invention may involve several of the following steps: transformation, isolation of epidermis, guard cell isolation, preparation of protoplasts from the guard cells, selection of transformants and regeneration of whole plants from the transformants. However, the order in which these steps may be performed may be varied and certain steps omitted, each variation having certain advantages.

1. Intact leaf tissue may be transformed, after which this material, or epidermis isolated therefrom is macerated to produce a cell suspension and then sonicated if necessary. The effect of these processes is to destroy preferentially cell types other than the guard cells. The concentration of guard cells, because of their comparative resistance to such physical stress, is enriched and they may thereafter be recovered by flotation or filtration from the suspension and whole plants regenerated.

2. In procedure 1 the inserted DNA construct may include a selectable marker gene, the more common ones being resistance to an antibiotic such as kanamycin or hygromycin or one of the herbicides such as BASTA. The leaf may then be exposed to selection pressure and only the surviving cells passed into suspension, or, alternatively, if the selection agent is added to the suspension of whole leaf tissue the viable guard cells which are recovered will comprise only transformed cells, obviating the need for a separate selection step.

However, it is preferred that the construct be entirely free of genes which specify antibiotic resistance. It is preferred, therefore that the selectable marker for the plant cells be the herbicide bialaphos. Selection at the bacterial stage of construct preparation preferably utilises the *Saccharomyces cerevisiae* IGPD gene (imidazole glycerol phosphate dehydratase) which is able functionally to complement mutant hisB strains of *E.coli* deficient in histidine biosynthesis, and restore their growth on minimal medium. Use of such an auxotrophic complementation system for recombinant selection obviates the requirement for bacterial antibiotic resistance markers, such as beta-lactamase, to be incorporated into plasmids for their manipulation in *E.coli* prior to their introduction into plant cells.

3. A suspension of guard cells may be prepared as described in 1 and the transformation carried out on the suspended cells. Vortexing with fibrous material such as silicon carbide whiskers is a convenient method in this case. The transformation may be effected before or after enrichment of the guard cell concentrate as described above and method 2 may additionally be used.

4. A guard cell suspension, or an enriched suspension, may be prepared as described above and the cells may be converted to protoplasts by enzymatic digestion before transformation. Plants may finally be regenerated from the protoplasts. Using protoplasts as the transformation target may allow certain known transformation techniques to be applied which may not be effective on the intact guard cells.

5. The simplest embodiment involves transformation of intact leaf or isolated epidermis, obtained either by mechanical means or manually, followed by regeneration under selection pressure. Since none of the cell types other than guard cells are known to be regenerable these will simply proliferate without regeneration, leaving the transformed guard cells to regenerate. Partially senescent leaves (containing predominantly only viable guard cells) may be particularly suitable.

The specific method for the introduction of the exogenous DNA construct is not particularly germane to this invention: it is a matter of convenience. However, we have achieved success in producing transgenic plants by the use of the known polyethylene glycol (PEG) mediated protoplast transformation procedure, followed by selection and regeneration.

The invention will now be described, by way of illustration, in the following Examples. The composition of the various media used in these Examples are given in Table 1 below.

TABLE 1

Medium A:
Half-strength MS medium *
3% sucrose
0.3% Gelrite (Trade Mark)
pH 5.8, autoclaved

* Murashige, T., Skoog, F., (1962) Physiologia Plantarum, 15, 473–497

Medium B:
9% mannitol
3.8% $CaCl_2.2H_2O$
0.1 mM n-propyl gallate
CPW salts **
pH 5.8, filter sterilised

** Frearson, E. M., Power, J. B., Cocking E. C. (1973), Developmental Biology, 33, 130–137

Medium C:
9% mannitol
0.1 mM n-propyl gallate
CPW salts **
2% Cellulase R-10 (Trade Mark)
3% Macerozyme R-10 (Trade Mark)
pH 5.8, filter sterilised

** Frearson, E. M., Power, J. B., Cocking E. C. (1973), Developmental Biology, 33, 130–137

Medium D:
9% mannitol
0.1 mM n-propyl gallate
CPW salts **
pH 5.8, filter sterilised
** Frearson, E. M., Power, J. B., Cocking E. C. (1973), Developmental Biology, 33, 130–137

Medium E:
15% sucrose
0.1 mM n-propyl gallate
CPW salts **
pH 5.8, filter sterilised
** Frearson, E. M., Power, J. B., Cocking E. C. (1973), Developmental Biology, 33, 130–137

Medium F:
9% mannitol
1 mM $CaCl_2.2H_2O$
filter sterilised

Medium G:
9% mannitol
1 mM $CaCl_2.2H_2O$
2% sodium alginate
autoclaved

Medium H:
7.25% mannitol
50 mM $CaCl_2.2H_2O$
0.9% Agarose (Trade Mark)
autoclaved Medium I:
1.5% Agarose
autoclaved Medium J:
6.84% glucose
0.1 mM n-propyl gallate
0.2 mg/l 2,4-dichlorophenoxyacetic acid (2,4-D)
1 mg/l naphthaleneacetic acid (NAA)
0.5 mg/l benzylaminopurine (BAP)
K8p medium (excluding sequestrene and casamino acids) ***
pH 5.8, filter sterilised
*** Kao, K. N., Michayluk, M. K. (1975), Planta, 126, 105–110

Medium K:
3% sucrose
0.8% Agarose
1 $\mu$M BAP
PGo medium ****
pH 5.8, autoclaved
**** De Greef, w., Jacobs, M., (1979) Plant Science Letters, 17, 55–61.

Medium L:
3% sucrose
0.8% Agarose
25 $\mu$M Indolebutyric acid (IBA)
PGo medium ****
pH 5.8, autoclaved
**** De Greef, w., Jacobs, M., (1979) Plant Science Letters, 17, 55–61.

EXAMPLE 1

Plant Material and Growth Conditions

[After Hall et.al., Plant Cell Reports 12: 339–342 (1993) and Pedersen et.al., Plant Science 95, 89–97 (1993)].

Aseptic shoot cultures of *Beta vulgaris* were obtained as follows: Seeds were sterilised by incubating for 50 minutes in $H_2SO_4$, after which they were thoroughly rinsed in tap water. The seeds were then placed in demineralised water at 55° C. for 15 minutes after which they were incubated in 5% sodium hypochlorite for 30 minutes. The sterilising solution was subsequently removed by rinsing three more times (5, 10 and 15 minutes) in sterile tap water.

Germination took place on water agar (1.5% agar in tap water) in the light at 22° C.

Sterile seedlings were cultured further on Medium A for 4 weeks before the meristems were removed for subculture on the same medium.

Shoots were subcultured every three weeks at which time the meristems were removed and placed on fresh medium. All cultures were incubated in the light (16 hour day, 3000 lux) at 22° C.

EXAMPLE 2

Leaf Protoplast Isolation

[After Krens et.al., Theoretical and Applied Genetics 79, 390–396 (1990)]

Protoplasts were isolated from the leaves of three week old aseptically-grown shoot cultures of *Beta vulgaris* as follows: Leaf blades were removed from shoot cultures and approximately 1.5 grams (dry weight) was finely chopped in 10 ml of Medium B in a 9 cm Petri dish.

After removal of Medium B, the leaf pieces were resuspended in 15 ml of Medium C containing the digestive enzymes.

Incubation took place in the dark on a rotary shaker (45 r.p.m., 11 mm amplitude) overnight (approximately 16 hours) at 25° C.

After gently pumping the crude protoplast mixture 10 times into and out of a pipette, the protoplast suspension was collected by gravity filtration through nylon sieves (297 and 55 $\mu$m mesh).

After placing the protoplast suspension in two 12 ml centrifuge tubes, the protoplasts were collected as a pellet by centrifugation at 55 g for 5 minutes.

The supernatant was discarded and the protoplasts were washed and centrifuged twice in 10 ml of Medium D.

Finally the protoplasts were resuspended in 10 ml of Medium E, on top of which there was carefully loaded 1 ml of Medium F, and centrifuged as above.

The protoplasts were collected from the upper 1 ml layer of Medium F and the population density determined using a haemocytometer.

All protoplast cultures were incubated at 25° C. in the dark.

EXAMPLE 3

Protoplast Embedding

[After Hall et.al., Plant Cell Reports 12, 339–342 (1993)]

Before culture, the protoplasts were immobilised as follows: A known number of protoplasts to give the desired plating density (usually 30,000–125,000 per dish) were resuspended in a total volume of 500 $\mu$l of Medium F.

After thorough mixing with 500 $\mu$l of Medium G, the suspension was spread out as a thin layer on to a 6 cm Petri dish containing 10 ml of Medium H.

After incubation for 2 hours at room temperature, the calcium alginate had solidified into a thin disc which was then removed and transferred to an empty Petri dish.

EXAMPLE 4

Fixation of the Immobilised Cells and Preparation of the Cultures for the Cell Finder To assist in the positioning and relocalisation of individual cells, the cultures were set up as follows: A 24.5×40 mm glass cover slip was sterilised in alcohol and flamed.

One drop (approximately 50 μl) of Medium I was spread over the entire surface of the cover slip and allowed to dry completely.

The central region (10×25 mm) of the calcium alginate disc was removed using a sharp scalpel.

One drop of Medium G was placed on the the cover slip, on top of which was placed the excised piece of the calcium alginate disc.

A ring of Medium I (35° C.) was placed around the edge of the alginate disc so that it came into contact with both the alginate and the agarose-covered glass cover slip.

Finally, using two drops of Medium I, two gold electron microscope specimen grids were fixed to the cover slip, one top centre and the other bottom right.

After solidification of the agarose, the entire assembly was transferred to a 6 cm Petri dish containing 4 ml of Medium J.

The remainder of the alginate disc was also transferred to this medium after which the dish was sealed with Parafilm (Trade Mark).

EXAMPLE 5

Cell Positioning and Relocation

A Zeiss ICM 405 inverted microscope equipped with a stepper motor driven microscope stage was used. A dedicated computer programme was used to control the movements of the microscope stage and to allow for system calibration and the recording of the position of individual cells in the Petri dish to an accuracy of 1 μm. Using the positions of the centres of the two EM grids at the fixed reference points, the positions of the cells of the desired size and morphology were located and recorded. At a later date, relocation of these cells was possible in a semiautomatic manner after the positions of the EM grids were re-entered into the computer for recalibration.

EXAMPLE 6

Cell Types Involved in Cell Division in Sugar Beet Leaf Protoplast Preparations Two subpopulations of protoplasts have been identified in beet leaf digests which have the capacity to divide and produce viable calli. These calli are, however, morphologically distinct and only one type is totipotent.

Callus of the regenerable type is characterised by being very soft, friable and watery which causes it to fall apart readily. The regeneration capacity of this type of callus varies, depending on the conditions and the genotype, but at its highest was 30%. The protoplasts identified as the progenitors of this callus type have a very distinct morphology, being relatively small, 15–27 (mode 23) μm in diameter, as measured after one day of culture in a medium with an osmolality of 510 mOs/kg. These cells contained few visible cytoplasmic components except for a small number of unusually large starch grains (usually 5–14 per cell with 8 or 9 per cell being most common). These starch grains might take up approximately 50% of the cell volume. Division of these cells occurs relatively late, 5–10 days after plating out and a loose-structured callus is produced which consists of small cells with a rich cytoplasm with many starch grains of varying size and shape. No obvious vacuole is visible.

The other type of callus is very hard and compact and usually forms spherical colonies. It appears not to be totipotent. This callus type has been found to originate from a protoplast type characterised by being 20–30 (mode 27) μm in diameter and rich in cytoplasm which contained many small and unevenly-sized and shaped starch grains. Typically these cells (as viewed one day after plating) already had a nucleus situated centrally in the cell. These cells divided early (usually within three days) and divided at a rapid rate to produce round compact colonies consisting of cells with a granular cytoplasm but with a clearly visible vacuole.

It has been confirmed, on the basis of morphological characters and by following partial epidermis digestions, that the first cell type, which gives rise to regenerable callus originates from the guard cells. It is believed that the second type is derived from cambial tissue from the vascular bundles. Mesophyll protoplasts never divide.

EXAMPLE 7

Isolation of Epidermis and Regeneration Peeling Method

Epidermal strips were obtained by manually peeling the lower epidermal side of leaves (in vitro material as well as greenhouse material), using curved forceps. This can be done in an empty Petri dish, on a piece of Whatman paper or in liquid medium (it does not really influence the division phase but is mainly based on personal preferences to get the largest strip out of one leaf). Neither the peeling angle nor the number of mesophyll cells which may remain influences the culture of the cells or the ability of the guard cells to divide.

Directly after the peeling, the strips are placed in culture medium. It does not matter which side of the strip is in contact with the medium. More important is the concentration of the strips per culture: the liquid surface should be covered for about 95% with strips after the isolation step. During culture, the strips will twist and coil and eventually sink but it has no effect on cell division.

Epidermal strips have been cultured in Petri dishes (5 and 20 cm diameter) and in microwells as long as the above mentioned condition was fulfilled. The strips were cultured at 28° C. in the dark.

Divisions were observed in several media: K8p, MS, PGo and BUL. However, the best is PGo medium which produced white friable callus in over 95% of the cultures. Most important was the fact that this medium does not contain hormones. Culture media containing hormones (BAP, NAA, 2,4-D) do not improve division frequencies. However, if 2,4-D is present in the culture medium (at concentrations from 0.2 to 2 mg/l) we observe a high concentration of hard type callus. As this callus cannot regenerate, and partially inhibits the production of the white friable callus, it is best to use PGo medium where no—or only very rarely—hard callus appears.

More than 30 different sugar beet genotypes were tested and all produced white friable callus at least once. The production of the white friable callus does not depend on the type of material (in vitro clone, seedling, greenhouse material) and neither does the medium on which this material has grown (MS, MS/2, PGo+BAP) influence the capacity of the guard cells to divide.

The epidermal strips are cultured in the dark at 28° C. for 4 to 5 weeks. The obtained white friable calli are transferred to PGo+BAP (1 mg/l) medium and further cultured in the same conditions for 3 to 4 weeks. This callus is then subcultured on the same medium or PGo+BAP (1 mg/l)+ NAA (0.2 mg/l) or on MS with the same two hormones at 20–22° C. with a light-dark cycle of 16–8 h. After two to three weeks the first regenerants can be recovered. We found the largest number of regenerants on the latter two media.

| BUL Medium | |
|---|---|
| | mg/liter |
| Macro | |
| $KNO_3$ | 2500 |
| $MgSO_4.7H_2O$ | 250 |
| $NaH_2PO_4.H_2O$ | 150 |
| $(NH_4)_2SO_4$ | 134 |
| $CaCl_2.2H_2O$ | 150 |
| Micro | |
| KI | 1.5 |
| $MnSO_4.H_2O$ | 20 |
| $H_3BO_3$ | 6 |
| $ZnSO_4.7H_2O$ | 4 |
| $Na_2MoO_4.2H_2O$ | 0.5 |
| $CuSO_4$ | 0.05 |
| $CoCl_2.6H_2O$ | 0.05 |
| $Na_2EDTA$ | 37.25 |
| $FeSO_4.7H_2O$ | 27.85 |
| Vitamins | |
| Thiamine | 2 |
| Pyridoxine | 6 |
| Nicotinic acid | 4 |
| B12 | 0.03 |
| Riboflavine | 1 |
| Ascorbic acid | 25 |
| Biotin | 2 |
| Folic acid | 1 |
| Choline chloride | 2 |
| Pantothenate | 2 |
| Casein hydrolysate | 500 |
| Sucrose | 30 g/liter |
| Hormones | |
| NAA | 1 |
| BAP | 0.2 |
| GA3 | 0.2 |
| Agar | 8 g/liter |

EXAMPLE 8

Epidermis Isolation—Blending Method

Manual peeling is very tedious and time consuming while the blending technique (as it is used in the protoplast isolation protocol) produces large amounts of small epidermal strips. But the blender is less selective as well as guard cells also produces also a lot of small debris of leaf tissue (and mainly cells that will produce hard type of callus).

Although in PGo medium we found the white type of callus on several occasions it is less consistent than with epidermal strips. On the other hand, it seems that the BUL medium is more appropriate.

In the protoplast isolation the blending is done in presence of Ficoll. To avoid the froth and to shorten the isolation time, we also worked directly with culture media (PGo and BUL) during the blending. Although BUL remains the best, good results were also obtained with PGo.

Epidermal strips, produced by the blending method were cultured in the same way as described in Example 3.

EXAMPLE 9

Guard Cell Protoplast Isolation and Culture

Epidermis fragments obtained by the method of Krens et.al., Plant Physiology, 90, 1382–1386 (1989), were digested overnight in a solution of 2% cellulase and 3% macerozyme dissolved in Medium D. However, different genotypes may require slightly different enzyme mixtures. After a washing and purification protocol as described in Example 2, protoplast populations were obtained which were highly enriched in guard cells. These methods have produced populations with up to 80–90% hguard cell protoplasts. Protoplasts were subsequently embedded in calcium alginate as detailed in Example 5 and were cultured in 4 ml of Medium J in a 6 cm Petri disk which was sealed with Parafilm. Cultures were incubated in darkness at 28° C. In these cultures, guard cell plating efficiencies of 25–50% were routinely obtained.

EXAMPLE 10

PEG-Mediated Genetic Transformation of Protoplasts

In this example the introduced DNA was from a plasmid pPG5 which contains the β-glucuronidase (GUS) reporter gene and also, as a selectable marker gene, a sequence specifying resistance to the herbicide Bialaphos or phosphinothricin to which sugar beet is normally sensitive.

The method employed was that described in Krens et.al., Nature, 296, 72–74 (1982 with the following selected parameters. The optimal concentration of PEG was 20% but lower concentrations also resulted in the production of stable transformants. The type of PEG was found not to be particularly significant. Stable transformants were found at all DNA concentrations tested but 50 μg/500,000 protoplasts was chosen as the optimal concentration. The period of incubation was from 10 to 40 minutes.

Table 2 below exemplifies some of the results obtained.

TABLE 2

| THE FREQUENCY OF STABLE TRANSFORMATION | | | | | |
|---|---|---|---|---|---|
| Sugar Beet Line | time min | Pps plated (% GC) | Bialaphos resistant calli | Trans. Freq. (total) | Trans. Freq. (GC) |
| NF | 10 | 180,000(74) | 22 | $1.2 \times 10^{-4}$ | $1.7 \times 10^{-4}$ |
| | 20 | 180,000(71) | 23 | $1.3 \times 10^{-4}$ | $1.8 \times 10^{-4}$ |
| | 30 | 83,000(54) | 28 | $3.4 \times 10^{-4}$ | $6.1 \times 10^{-4}$ |
| SES1 | 20 | 220,000(80) | 8 | $2.7 \times 10^{-5}$ | $3.4 \times 10^{-5}$ |
| | 30 | 190,000(85) | 1 | $5.3 \times 10^{-6}$ | $6.2 \times 10^{-5}$ |
| | 40 | 210,000(76) | 4 | $1.9 \times 10^{-5}$ | $2.5 \times 10^{-5}$ |

In all the above cases the PEG concentration was 13.3% and the amount of DNA (pPG5) used was 50 μg.

Following transformation, the protoplasts were transferred to an alginate medium containing bialaphos at a concentration of 0.25 mg/liter, and cultured for four weeks, by which time the transformed guard cell calli were clearly identifiable and could be isolated and transferred to regeneration medium.

EXAMPLE 11

Genetic Transformation of Leaf Tissue

In this example the introduced DNA was from a plasmid pPG5 which contains the β-glucuronidase (GUS) reporter gene and also, as a selectable marker gene, a sequence specifying resistance to the herbicide Bialaphos or phosphinothricin to which sugar beet is normally sensitive.

Leaves from axenically grown plants of two sugar beet genotypes (designated BOA113 and BUM2) were excised and placed, abaxial surface uppermost, on De Greef and Jacobs media solidified with 0.6% agar. Three to five leaves were used in each 9 cm Petri dish.

Gold particles (1.6 μm diameter) were coated with a plasmid which contains a gene encoding phosphinothricin acetyl transferase which gives resistance to the herbicide phosphinothricin (bialaphos, BASTA) as a selectable marker and one copy of a gene encoding β-glucuronidase (gus), a detectable marker gene. The particles were coated using the calcium chloride/spermidine precipitation method and resuspended in 100% ethanol. Aliquots of 10 μl were pipetted on to individual macrocarriers of the DuPont Biolistic PDS1000/He gene gun and allowed to dry over silica gel crystals.

The bombardment parameters used were: a gap of one sixteenth inch between the rupture disc and the macrocarrier, a macrocarrier travel distance of 6 mm, rupture disc pressures of 100 to 1100 psi, target distances of 5, 8 or 12 cm and a partial vacuum of 28 inches of mercury in the target chamber.

After bombardment, leaves were cultured for 2 days at 23° C. prior to staining with 5-bromo-4-chloro-3-indolyl-β-D-glucuronide (X-Gluc) for histochemical localisation of gus gene expression. Post staining, the leaves were decolourised in 95% ethanol at 65° C. for 20 minutes. Cells showing gus expression were termed "colour-forming units" (CFUs). The frequency of guard cell CFUs among total epidermal CFUs for both genotypes was in the range 20–40%.

EXAMPLE 12

Callus Culture and Regeneration

After 21 days, the pieces of alginate containing the now-visible microcalli were transferred to 9 cm Petri dishes containing 20 ml Medium K. Culture was in the dark as above.

Friable, watery-type calli on reaching the size of approximately 1–2 mm in diameter were individually picked off and cultured in groups of 20 on fresh Medium K. At this stage both PCR analysis and a histochemical GUS assay confirmed the presence of transformants.

At two-weekly intervals all calli were subcultured on to fresh medium.

Regenerants appeared during the first 8 weeks of culture of individual calli. When the first shoots were visible and had reached a size of approximately 2 mm the dish was transferred into the light (3000 lux), 25° C., 15 hour day length.

Plantlets approximately 4 mm long were transferred to individual culture tubes containing 15 ml of Medium K and were further subcultured in the light as above.

EXAMPLE 13

Rooting and Transfer to the Soil

When the plantlets had reached the four-leaf stage (usually after 5 to 6 weeks with one subculture after three weeks) they were transferred to culture tubes containing 15 ml of Medium L and further cultured as above.

When at least one root had reached a length of 1 cm, the plantlets were removed from the culture tubes and, washed under running tap water to remove all fragments of the agar, and transferred to soil in 9 cm pots in the greenhouse.

Plantlets were covered with a transparent plastic cup to provide a humid environment for seven days, after which they could be grown without protection.

We claim:

1. A method of producing a *Beta vulgaris* plant, comprising culturing isolated *Beta vulgaris* stomatal cells in a regeneration medium and regenerating a *Beta vulgaris* plant from the thus cultured cells.

2. The method of claim 1, wherein the plant is sugar beet.

3. The method of claim 1, wherein the regeneration includes the production of callus on a medium which is free of hormones.

4. A method for the genetic transformation of a *Beta vulgaris* plant comprising introducing an hereditary material into an isolated stomatal cell of said plant or a cell population enriched in guard cells and regenerating whole plants from the transformed cell or population.

5. The method of claim 4, wherein the said population is contained within a senescent leaf.

6. The method of claim 4, wherein the stomatal cell is obtained from macerated tissue.

7. The method of claim 4, wherein the stomatal cell is converted to a protoplast prior to regeneration.

8. The method of claim 4, in which the hereditary material is a DNA construct which includes a selectable marker gene which does not specify resistance to an antibiotic and the transformed cell is exposed to an appropriate selective agent.

9. The method of claim 4, wherein the transformation is conducted on a cell population enriched in guard cells.

10. The method of claim 4, wherein the stomatal cells are converted into protoplasts by enzymatic digestion of the cell wall before or after transformation.

11. The method of claim 4, wherein transformation is effected by mixing a suspension of stomatal cells with a microscopic fibrous material and agitating same in the presence of the hereditary material.

12. The method of claim 4, wherein the regeneration includes the production of callus on a medium which is free of hormones.

13. The method of claim 4, wherein the hereditary material is a DNA construct which does not contain a gene specifying antibiotic resistance.

\* \* \* \* \*